US012349993B2

(12) United States Patent
Giersch et al.

(10) Patent No.: US 12,349,993 B2
(45) Date of Patent: Jul. 8, 2025

(54) DEVICE FOR COMPUTER-ASSISTED SURGERY HAVING TWO ARMS AND METHOD FOR OPERATING THE SAME

(71) Applicant: Stryker European Operations Limited, Carrigtwohill (IE)

(72) Inventors: Helge Giersch, Laboe (DE); Manfred Wieland, Kiel (DE); Ole Prien, Kiel (DE); Hannemann Knut, Pinneberg (DE)

(73) Assignee: Stryker European Operations Limited, Carrigtwohill (IE)

( * ) Notice: Subject to any disclaimer, the term of this patent is extended or adjusted under 35 U.S.C. 154(b) by 247 days.

(21) Appl. No.: 17/912,197

(22) PCT Filed: Mar. 19, 2020

(86) PCT No.: PCT/IB2020/052523
§ 371 (c)(1),
(2) Date: Sep. 16, 2022

(87) PCT Pub. No.: WO2021/186218
PCT Pub. Date: Sep. 23, 2021

(65) Prior Publication Data
US 2023/0131337 A1    Apr. 27, 2023

(51) Int. Cl.
*A61B 34/30*    (2016.01)
*A61B 17/16*    (2006.01)
(Continued)

(52) U.S. Cl.
CPC ............ *A61B 34/30* (2016.02); *A61B 17/164* (2013.01); *A61B 17/1703* (2013.01); *A61B 2034/2068* (2016.02); *A61B 2034/306* (2016.02)

(58) Field of Classification Search
CPC ... A61B 34/30; A61B 17/164; A61B 17/1703; A61B 2034/2068; A61B 2034/306
(Continued)

(56) References Cited

U.S. PATENT DOCUMENTS 11,253,323 B2 *  2/2022  Hughes .................. A61B 34/10
11,931,267 B2 *  3/2024  Wilde .................... A61F 2/4603
(Continued)

FOREIGN PATENT DOCUMENTS

EP    3494918 A1    6/2019
WO    9500085 A1    1/1995
(Continued)

OTHER PUBLICATIONS

International Search Report for Application No. PCT/IB2020/052523 mailed Dec. 18, 2020, pp. 1-5.
(Continued)

*Primary Examiner* — Kira Nguyen
(74) *Attorney, Agent, or Firm* — Lerner David LLP

(57) ABSTRACT

Computer-assisted surgery device and a method for operating the same which allows a more efficient positioning and application of an implant with respect to a bony structure, and in particular a shorter operation time and less intensity of x-ray exposure for a patient. A device for computer-assisted surgery includes a reference structure, a first arm, a second arm, a position determining unit and a motion controlling unit.

20 Claims, 6 Drawing Sheets

(51) Int. Cl.
*A61B 17/17* (2006.01)
*A61B 34/20* (2016.01)

(58) Field of Classification Search
USPC .......................................... 700/245
See application file for complete search history.

(56) References Cited

U.S. PATENT DOCUMENTS

| | | | |
|---|---|---|---|
| 2004/0143184 A1* | 7/2004 | Kienzle, III | A61B 34/20 600/427 |
| 2005/0288679 A1* | 12/2005 | Kienzle, III | A61B 34/20 606/97 |
| 2010/0274256 A1 | 10/2010 | Ritchey et al. | |
| 2016/0302871 A1* | 10/2016 | Gregerson | A61B 6/547 |
| 2017/0258535 A1 | 9/2017 | Crawford et al. | |
| 2019/0167356 A1* | 6/2019 | Britton | A61B 90/50 |

FOREIGN PATENT DOCUMENTS

| | | | |
|---|---|---|---|
| WO | 2016196165 A1 | 12/2016 | |
| WO | 2017064301 A1 | 4/2017 | |

OTHER PUBLICATIONS

Communication pursuant to Article 94(3) EPC, for European Application No. 20728183.3, dated Feb. 26, 2025, pp. 1-6.

\* cited by examiner

DEVICE FOR COMPUTER-ASSISTED SURGERY HAVING TWO ARMS AND METHOD FOR OPERATING THE SAME

CROSS-REFERENCE TO RELATED APPLICATIONS

The present application is a national phase entry under 35 U.S.C. § 371 of International Application No. PCT/IB2020/052523 filed Mar. 19, 2020, the disclosures of which are hereby incorporated by reference herein.

FIELD OF THE INVENTION

The present invention relates to a computer-assisted surgery device and a method for operating the same which allows a more efficient positioning and application of a sub-implant or tool or guiding device for guiding a tool, drill or K-wire with respect to a main-implant, and in particular to a computer-assisted surgery device having two robot arms and a method for operating the same resulting in a less intensity of x-ray exposure.

BACKGROUND OF THE INVENTION

For applying an implant to a body of a patient, in particular to a bony structure of a patient, it is required to make sure that the implant position with respect to the bony structure is correct, so that the patient does not suffer from a misalignment of the implant. This is in particular relevant for implants for legs, as a misalignment of implants in the leg, in particular on the hip, the knee or the ankle, may result in a serious limitation of patient's mobility, in particular the walking capabilities.

Applying an implant to a patient, in particular to a bony structure of a patient, therefore requires a sufficient monitoring of the application and the alignment of the implant with respect to the bony structure. In the past, this was achieved by a repeated monitoring of the situation by taking a plurality of x-ray images illustrating the present implanting situation between the implant and the bony structure, so that the surgeon, based on the respective x-ray imaging, could re-align the implant to the bony structure repeatedly unless the implant has arrived at the desired position and alignment with the bony structure. This may have lead to a repeated, i.e. higher x-ray exposure of the patient, which may have had undesired effects for the patient.

In the past, it was also usual for a surgeon to place a K-wire tip to the outside of the bone or to insert the K-wire a few cm, so that a better illustration was possible. Nevertheless, also this approach required a large number of iterations including a large number of x-ray images with a high radiation and at the same time a limited accuracy.

In the past, also applications were known where a full navigation system was used which required trackers on the relevant bone fragments and instruments as well as a full navigation setup with a stereo camera, which also resulted in a high x-ray exposure.

In view of the above, there was a need for providing a device and a method for operating the device allowing a high accuracy and a reduced x-ray exposure over the previously known devices and methods.

SUMMARY OF THE INVENTION

The present invention provides a device for computer-assisted surgery having two robot arms and a method for operating the same according to the subject-matter of the independent claims, providing a more exact positioning of an implant and a sub-implant, tool, drill od K-wire with respect to each other and less x-ray exposure. Further embodiments of the invention are incorporated in the dependent claims.

According to an aspect of the invention there is provided a device for computer-assisted surgery comprising a reference structure; a first arm having a first end and a second end, wherein the first arm with the first end is connected to the reference structure and with the second end is connectable to a main-implant in a defined geometrical orientation; a second arm having a first end and a second end and a plurality of segments, wherein at least two adjacent segments are coupled with a joint being capable of being controllably brought from a fixed state into a released state and vice versa, wherein the second arm with the first end is connected to the reference structure and with the second end is connectable to a tool in a defined geometrical orientation with respect to a tooling trajectory of the tool; a position determining unit being adapted for determining a required position and orientation of the connected tool having the tooling trajectory for bringing the tooling trajectory of the tool into a direction, so that the tooling trajectory of the tool corresponds to a joining portion of the main-implant with the tool; a motion controlling unit being adapted for bringing the second arm from the fixed state into the released state, for controlling a motion of the second arm based on a measure of required motion determined by the position determining unit, and for bringing the second arm from the released state into the fixed state.

Thus, it is possible to provide a device for computer-assisted surgery allowing to coordinate the implantation of an implant as well as the positioning of a tooling device with respect to the implanted implant, which may be useful for example when applying a locking screw to the implant through a traverse borehole of the implant. As the device does not only provide arms for supporting an implant and a tool, but also is capable of determining the geometrical orientation of the implant and the tool, and to determine the relative geometrical orientation with respect to each other, it is possible to determine the required motion so that a tooling trajectory of the tool meets the joining portion of the implant, which then for example receives a sub-implant in form of, for example, a locking screw. The relative geometrical orientation/position can be determined by using a reference structure to which the arms are mounted. A reference structure can be understood as a reference to which the first arm and the second arm are mounted with their respective second ends, so that when knowing the relative position/orientation of a first end and a respective second end of an arm, also the relative position/orientation of both first ends of the arms can be determined. It should be understood, that the reference structure does not need to be a single point but also may be a fixed structure where the first arm is mounted to a first area of the structure and the second arm is mounted to a distant area at this structure for example. Such a structure may for example be a structure where a patient can be located during applying positioning of an implant and a tooling device or a sub-implant. When knowing the geometry of the structure, in particular the both connecting points to which the second ends of the arms are connected, as well as the relative position/orientation of the both arms, in particular the relative position/orientation of their first and second ends, also the relative position/orientation of their respective first ends and thus the relative position/orientation of the connected devices can be determined. As the device also includes a motion controlling unit, the surgeon does not need to bring the tool into the respective position. Motion controlling may include providing the surgeon with the information to which extend the second arm, in particular the second end of the second, segmented arm with the tooling device, is to be moved to achieve the desired alignment. This in particular applies for jurisdictions, where it is not allowed to let the device doing an interaction with the patient, but only a surgeon. Motion controlling may also include controlling the motion of the arm by actuators. In the latter case, the task of the surgeon only remains the monitoring of the positioning and motion of the device. This will lead to a more exact procedure conducted by the device and further reduce the x-ray exposure, which would be necessary if a surgeon would take over, without an inventive device, the positioning in an iterative process while iteratively taking x-ray images for checking whether the correct position of the tool with respect to the implant is achieved.

According to a further aspect of the invention, there is provided a device for computer-assisted surgery comprising a reference structure; a first arm having a first end and a second end, wherein the first arm with the first end is connected to the reference structure and with the second end is connectable to a main-implant in a defined geometrical orientation; a second arm having a first end and a second end and a plurality of segments, wherein at least two adjacent segments are coupled with a joint being capable of being controllably brought from a fixed state into the released state and vice versa, wherein the second arm with the first end is connected to the reference structure and with the second end is connectable to a sub-implant in a defined geometrical orientation with respect to an implantation trajectory of the sub-implant; a position determining unit being adapted for determining a required position and orientation of the connected sub-implant having the implantation trajectory for bringing the implantation trajectory of the sub-implant into a direction, so that the implantation trajectory of the sub-implant corresponds to a joining portion of the main-implant with the sub-implant; and a motion controlling unit being adapted for bringing the second, segmented arm from the fixed state into the released state, for controlling a motion of the second, segmented arm based on a measure of required motion determined by the position determining unit, and for bringing the second arm from the released state into the fixed state.

Thus, it is possible to not only bring a tool into the correct tooling orientation with respect to an implant, but also to bring a sub-implant like, for example, a locking screw into the correct orientation, so that the sub-implant's trajectory meets the joining portion of the main-implant.

As described above, the surgeon no longer needs to determine the relative position of the sub-implant with respect to the main-implant. Moreover, the device takes over the determination of the relative position and the required motion to bring the sub-implant into an orientation and position so that a trajectory of the sub-implant meets the joining portion of the main-implant. As the device also takes over the motion controlling, the surgeon no longer needs to bring the sub-implant into the correct position and orientation with respect to the implant, as this is done by the device. Thus, also no iterative x-ray exposure takes place, compared to a situation, where the surgeon iteratively re-positions a sub-implant with respect to an implant and monitors the iterative re-positioning by taking x-ray images after each iterative re-positioning step. Motion controlling may include providing the surgeon with the information to which extend the second arm, in particular the second end of the second arm with the sub-implant, is to be moved by the surgeon to achieve the desired alignment. Motion controlling may also include controlling the motion of the arm by actuators. In the latter case, the task of the surgeon only remains the monitoring of the positioning and motion of the device. The surgeon may monitor the entire process conducted by the device, so that a positioning of a sub-implant with respect to an implant can be achieved in a more reliable way with a reduced x-ray exposure compared to the manual process conducted by a surgeon.

According to a further aspect of the invention, there is provided a device for computer-assisted surgery, comprising a reference structure; a first arm having a first end and a second end, wherein the first arm with the first end is connected to the reference structure and with the second end is connectable to a main-implant in a defined geometrical orientation; a second arm having a first end and a second end, wherein the second arm with the first end is connected to the reference structure and with the second end is connectable to a guiding device in a defined geometrical orientation with respect to a guiding trajectory of the guiding device; an identification unit being adapted for identifying a main implant with a joining portion being connected to the second end of the first arm; a position determining unit being adapted for determining a required position and orientation of a connected guiding device having the guiding trajectory based on a stored geometry of the identified main implant and its joining portion for bringing the guiding trajectory of the guiding device into a direction, so that the guiding trajectory of the guiding device corresponds to a joining portion of the main-implant with a device to be guided; a motion controlling unit being adapted for controlling a motion of the second arm based on a stored geometry of the identified main implant and its joining portion and a measure of required motion determined by the position determining unit for bringing the guiding trajectory of the guiding device into a direction, so that the guiding trajectory of device to be guided corresponds to a joining portion of the main-implant with device to be guided.

Thus, it is possible to not only bring a tool or sub-implant into the correct tooling orientation with respect to an implant, but also to bring a guiding device, for example a sleeve, into the correct orientation, so that the guiding trajectory of the guiding device meets the joining portion of the main-implant. It is possible to identify a main implant and based on geometrical information of the main implant to align the guiding trajectory of the guiding device to a joining portion of the main-implant. The guiding device may guide a drill, which is operated by a surgeon, so that the drill drills along an axis, which meets the joining portion of the main implant. As described above, the surgeon no longer needs to determine the relative position of the guiding device and thus the guided devices, like a drill or a K-wire, with respect to the main-implant. Moreover, the device takes over the determination of the relative position and the required motion to bring the guiding device and the guided device into an orientation and position so that a trajectory of the guiding device and the guided device meets the joining portion of the main-implant. As the device also takes over the motion controlling, the surgeon no longer needs to bring the guiding device into the correct position and orientation with respect to the implant, as this is done by the device. Thus, also no iterative x-ray exposure takes place, compared to a situation, where the surgeon iteratively re-positions a guiding device with respect to an implant and monitors the iterative re-positioning by taking x-ray images after each iterative re-positioning step. Motion controlling may include providing the surgeon with the information to which extend the second arm, in particular the second end of the second arm with the guiding device, is to be moved to achieve the desired alignment. Motion controlling may also include controlling the motion of the arm by actuators. In the latter case, the task of the surgeon only remains the monitoring of the positioning and motion of the device. The surgeon may monitor the entire process conducted by the device, so that a positioning of a guiding device with respect to an implant can be achieved in a more reliable way with a reduced x-ray exposure compared to the manual process conducted by a surgeon.

According to a further aspect of the invention, there is provided a device for computer-assisted surgery, comprising a reference structure; a first arm having a first end and a second end wherein the first arm with the first end is connected to the reference structure and with the second end is connectable to a main-implant in a defined geometrical orientation; a second arm having a first end and a second end, wherein the second arm with the first end is connected to the reference structure and with the second end is connectable to a tool in a defined geometrical orientation with respect to a tooling trajectory of the tool; an identification unit being adapted for identifying a main implant with a joining portion being connected to the second end of the first arm; a position determining unit being adapted for determining a required position and orientation of a connected tool having the tooling trajectory based on a stored geometry of the identified main implant and its joining portion for bringing the tooling trajectory of the tool into a direction, so that the tooling trajectory of the tool corresponds to a joining portion of the main-implant with the tool; a motion controlling unit being adapted for controlling a motion of the second arm based on a stored geometry of the identified main implant and its joining portion and a measure of required motion determined by the position determining unit for bringing the tooling trajectory of the tool into a direction, so that the tooling trajectory of the tool corresponds to a joining portion of the main-implant with the tool.

According to a further aspect of the invention, there is provided a device for computer-assisted surgery, comprising a reference structure; a first arm having a first end and a second end, wherein the first arm with the first end is connected to the reference structure and with the second end is connectable to a main-implant in a defined geometrical orientation; a second arm having a first end and a second end, wherein the second arm with the first end is connected to the reference structure and with the second end is connectable to a sub-implant in a defined geometrical orientation with respect to an implantation trajectory of the sub-implant; an identification unit being adapted for identifying a main implant with a joining portion being connected to the second end of the first arm; a position determining unit being adapted for determining a required position and orientation of a connected sub-implant having the implantation trajectory based on a stored geometry of the identified main implant and its joining portion for bringing the implantation trajectory of the sub-implant into a direction, so that the implantation trajectory of the sub-implant corresponds to a joining portion of the main-implant with the sub-implant; a motion controlling unit being adapted for controlling a motion of the second arm based on a stored geometry of the identified main implant and its joining portion and a measure of required motion determined by the position determining unit for bringing the implanting trajectory of the sub-implant into a direction, so that the implantation trajectory of the sub-implant corresponds to a joining portion of the main-implant with the sub-implant.

Thus, it is possible to identify an implant and based thereon to control the device, in particular a robot arm, which operates a tool or a sub-implant, which is to be joint with a joining portion of the main implant. Once the main implant is identified, corresponding geometrical data can be achieved from a database, so that robot exactly knows the position and orientation of a joining portion of the main implant, e.g. an intramedullary nail, in order to exactly position a tool, e.g. a drill, or a sub-implant, e.g. a locking screw for an intramedullary nail. A targeting device at the second end of a robot arm may have a coupling geometry, which exactly defines the position and orientation of an implant, sub-implant or tool.

However, the coupling geometry may be designed to receive a plurality of different instruments, implants, sub-implants or tools. As the geometry of the robot arm with the connected targeting device can be determined based on the known geometries of the robot arm, its fixation to a reference structure and sensed positions of segments of an robot arm, the relative position of a targeting device or coupling geometry with respect to the reference structure is known or can be determined based on position sensor data. The position of the joining portion of a main implant, e.g. a borehole for receiving a locking screw, is known from the defined geometry of the main implant, e.g. an intramedullary nail. Consequently, also the relative position and orientation of the joining portion with respect to the reference structure can be determined. If the main implant is exchanged, the geometry of the robot arm remains the same. In case the geometry of the main implant can be achieved from a data base, the relative position and orientation of the joining portion can be determined based thereon.

According to an embodiment of the invention, the identification unit is connected to a human interface for entering a main implant identifier allowing the identification unit to identify the main implant with its joining portion and its corresponding geometry from a database.

Thus, it is possible to feed the device with information on which implant is used. It should be noted that the input by a user can be given by entering an identification code of the implant or selecting a main implant from a menu on a graphical user interface. The device may pre-select main implants, which fit to a particular patient. The same applies for the sub-implant.

The user may select a sub-implant by entering an identification number or the like, or by selecting a sub-implant from a menu on a graphical user interface. The device may also pre-select the sub-implants, e.g. sub-implant which fit for the previously selected main-implant. The same also applies for a selected tool, e.g. a drill, so that a user can select a drill out of e.g. a menu, but only tools, which previously were defined to be used in combination with the particular implant or sub-implant. Respective software may be applied or downloaded which is required for a particular action of combining a main implant and sub-implant, or main-implant and tool, e.g. a software including drilling instructions. The device may have stored a variety of different software modules for this purpose, or may download the required program from a data base or via a network.

According to an embodiment of the invention, the identification unit is connected to an image acquiring unit for receiving imaging data of a connected main implant, wherein the identification unit comprises an image recognition unit being adapted for recognition and identification of the main implant for identifying the main implant with its joining portion and its corresponding geometry from a database.

Thus, it is possible to automatically identify the used main-implants, sub-implants or tools. This also allows a monitoring, whether the selected main-implant matches a sub-implant or a tool, and to warn the user or surgeon on an erroneous selection. The image recognition can also be used to perform the above described pre-selection.

According to an embodiment of the invention, the second arm has a plurality of segments, wherein at least two adjacent segments are coupled with a joint being capable of being controllably brought from a fixed state into a released state and vice versa, wherein the motion controlling unit being adapted for bringing the second arm from the fixed state into the released state for controlling a motion of the second arm based on a measure of required motion determined by the position determining unit, and for bringing the second arm from the released state into the fixed state.

Thus, in particular in combination with the identification of the main-implant, the sub-implant or the tool, the arm of the robot, be it the first arm with the main-implant connected thereto, or the second arm with the sub-implant or tool connected thereto, it is possible to stabilize the robot arm after positioning. Thus, the implantation trajectory or tooling trajectory, once the arm is brought into the fixed or locked state, cannot be changed by accident. The segments of the in particular second arm are coupled with a joint which may be brought from a fixed state into a released state and vice versa, wherein a fixed state is understood as a state where two adjacent segments have a fixed position and orientation with respect to each other. A released state can be understood as a state where two adjacent segments can be moved along at least one degree of freedom, wherein the number of degrees of freedom is not limited for the purpose of the invention. Bringing the joint from a fixed state to a released state and vice versa may be achieved by providing a locking mechanism to lock the joint in a fixed state and may also be achieved by providing a driving mechanism for moving the adjacent segments with respect to each other, which maintains its position and orientation when it does not receive any driving instructions. The reference structure can be understood as a reference point to which the first arm and the second arm is mounted. It should be understood, that the reference structure does not need to be a single point but also may be a fixed structure where the first arm is mounted to a first area of the structure and the second arm is mounted to a distant area at this structure for example. Such a structure may for example be a structure where a patient can be located during applying positioning of an implant and a tooling device or a sub-implant.

According to an embodiment of the invention, the first arm and the second arm at their connecting joints between respective segments and between the first and second arm and their respective reference structure have position sensors being capable of providing positional information allowing determining the relative position of the second end of the first arm and the second end of the second arm with respect to each other.

Thus, a feedback, in particular a permanent feedback, can be achieved on the respective position and orientation of the segments of both arms, so that a relative position and orientation of the end of the first arm to which an implant is connected and an end of the second arm to which a sub-implant or a tooling device is connected can be determined and monitored. If providing sensors at each of the connecting joints, from the entirety of the sensed position and orientation data, the resulting orientation and position data of the main-implant and the sub-implant or the tooling device and/or tool may be derived.

According to an embodiment of the invention, the first arm has at least two segments and a connecting joint between the two adjacent segments, wherein the connecting joint is capable of being controllably brought from a fixed state into a released state and vice versa.

Thus, not only the second arm, but also the first arm may be provided with connecting joints, which allows a more flexible handling of the first arm to which an implant can be mounted.

According to an embodiment of the invention, the first arm has at least one actuator, each being adapted to controllably actuate a motion of two adjacent segments with respect to each other along the connecting joint of two adjacent segments.

Thus, it is not only possible to control the position and orientation of the segments of the second arm, but also to control the motion of the first arm in order to actuate the positioning of the implant, which is mounted to the first arm.

According to an embodiment of the invention, the second end of the first arm has a reference geometry connected thereto and the second end of the second arm has a reference geometry connected thereto.

Thus, it is possible to detect the respective ends of the first arm and the second arm based on their respective reference geometries. As an implant is usually fixed in a defined manner to the second end of the first arm, also the position and the orientation of the implant can be determined based on the position and orientation of the reference geometry of the first arm. In the same manner, as a sub-implant or a tool or a guiding device also is usually mounted in a defined manner to the second end of the second arm, the position and orientation of a sub-implant or a tool or a guiding device can be determined based on the position and orientation of a reference geometry provided at the second arm. As a consequence, also the relative position and orientation of the main-implant and the sub-implant or tool or guiding device can be determined from an x-ray image, so that the relative position determined from the sensors can be compared and verified by the relative position determined from the x-ray image.

According to an embodiment of the invention, at least one of the reference geometries has a unique projection pattern for each projection direction.

Thus, a reference geometry, when illustrated on an x-ray image, may be used as a basis for determining the position and orientation of the respective end of the first and second arm as well as the position and orientation of an implant, a sub-implant or a tooling device or guiding device. It should be noted, that although the entire situation may also be illustrated by a three-dimensional x-ray imaging, the unique projection pattern of the reference geometries allows the determination of the position and orientation thereof based on only a single two-dimensional x-ray image. However, it should be noted, that taking a plurality of x-ray images may increase the redundancy and thus the safety when determining the position and orientation of the implant, sub-implant and tooling device.

According to an embodiment of the invention, at least one of the reference geometries has a plurality of fiducial markers, wherein the fiducial markers have a spatial arrangement having a unique projection pattern for each projection direction.

Fiducial markers are usually provided in form of small spheres, so that a clear distinction over the background is possible in an x-ray image. The arrangement of the plurality of fiducial markers may provide an efficient way to detect and identify the fiducial markers in an x-ray image in order to provide an easy and reliable determination of the position and orientation of the reference geometry and thus of the implant, the sub-implant, guiding device or tooling device and/or tool. However, it should be noted that in case the reference geometry does not have fiducial markers, but only a unique projection for each projection direction, a more advanced image recognition may be used to identify the position and orientation of the reference geometry. As fiducial markers usually have a better contrast, image recognition may be reduced to the recognition of clear and contrasted dots in an x-ray image.

According to an embodiment of the invention, the guiding device comprises a sleeve having a longitudinal through hole defining the guiding trajectory of the guiding device.

Thus, the longitudinal though hole may serve as a reliable guide for e.g. a drill or a K-wire. With this respect, a K-wire is a wire or pin, which is sharpened and widely used in orthopedics and other types of medical surgery. They are used to hold bone fragments together (pin fixation) or to provide an anchor for skeletal traction. K-wires are often driven into the bone through the skin (percutaneous pin fixation) using a power or hand drill.

According to an embodiment of the invention, the guiding device is adapted to guide a K-wire or to guide a drill.

According to an embodiment of the invention, the device for computer assisted surgery further comprises a deviation determining unit being capable of determining a spatial deviation of a present relative position of the guiding device and one of a K-wire and a drill guided by the guiding device and a spatial deviation of an intended relative position of the guiding device and one of a K-wire and a drill guided by the guiding device based on reference geometries provided with the guiding device, the K-wire to be guided and the drill to be guided.

Thus, it is possible to recognize reference geometries of the used devices, i.e. the guiding device and the guided device, for example a reference geometry of a sleeve and the reference geometry of a drill. By recognizing reference geometries, e.g. in an x-ray image, the spatial position of e.g. a sleeve and a drill can be determined, so that it can be determined how far a drill has entered the location. Not only the spatial position of the sleeve and the drill with respect to each other can be determined, but also between the drill and the main implant. Instead of the drill, also the position of a K-wire may be recognized and determined accordingly.

According to an embodiment of the invention, the tool is a drilling tool or a guiding sleeve for a drill and the tooling trajectory is a drilling direction toward a joint of the main-implant.

Thus, the device can be used to drill a hole in a bony structure for receiving for example a locking screw as a sub-implant to be inserted into a joint hole of the main-implant and to achieve that the borehole through the bony structure perfectly aligns with the through hole of a joining portion of the main-implant. The drilling can be done by the device itself, e.g. by providing a drill and a drive for driving the drill at the second end of the robot arm and controlling the drill process by the device. Once the robot arm has arrived at the desired position with respect to the aligned drilling trajectory, the device itself may start drilling the drill toward the drilling trajectory, e.g. to generate a bore hole in a bony structure in alignment with a joining portion of the main implant in form of a through hole in the main implant. The drilling can also be done manually by a user or surgeon.

In the latter case the tool may be designed as a guiding sleeve for a drill, so that a surgeon may use a manually held drilling machine with a drill, wherein the drill is guided through the guiding sleeve in order to predefine the drilling trajectory. Once the robot arm has arrived at the desired position with respect to the aligned drilling trajectory, the surgeon may start drilling the drill with e.g. a hand held drilling machine toward the drilling trajectory, e.g. to generate a bore hole in a bony structure in alignment with a joining portion of the main implant in form of a through hole in the main implant.

According to an aspect of the invention, there is provided a method for operating a computer-assisted surgery device comprising providing a reference structure; connecting to a first arm having a first end and a second end at the second end a main-implant in a defined geometrical orientation, wherein the first arm with the first end is connected to the reference structure; connecting to a second arm having a first end and a second end and a plurality of segments, at the second end a tool in a defined geometrical orientation with respect to a tooling trajectory of the tool, wherein at least two adjacent segments are coupled with a joint being capable of being controllably brought from a fixed state into a released state and vice versa, wherein the segmented second arm with the first end is connected to the reference structure; determining a required position and orientation of the connected tool having the tooling trajectory for bringing the tooling trajectory of the tool into a direction, so that the tooling trajectory of the tool corresponds to a joining portion of the main-implant with the tool; bringing the second arm into the released state; controlling a motion of the second, segmented arm based on the determined required motion; bringing the second arm from the released state into the fixed state; and operating the tool toward the tooling trajectory.

Thus, it is possible to operate a computer-assisted surgery device in a manner, so that a tool, for example drilling a through-hole through a bony structure, is positioned such that it meets the position and orientation of, for example, a through-hole in a main-implant. This allows that later, for example, a locking screw can be positioned in the borehole of the bony structure and the aligned through-hole of the main-implant. The method thus allows making sure, that the implant as well as the tool, which is required for positioning of a sub-implant, are correctly positioned with respect to each other. Thus, the surgeon does no longer need to position the tool in a correct position and orientation with respect to the main-implant, as the method takes over this operation when operating the computer-assisted surgery device.

Therefore, it can be avoided that a surgeon in a trial and error procedure iteratively re-positions a tool with respect to an implant. Controlling movement may be providing the surgeon with information to which extend the second arm with the sub-implant or tool is to be moved, or to directly actuate actuators of the respective arm of the device. The method for operating the computer-assisted surgery device thus may increase the exactness of the positioning as well as reduce the required time therefore. As the surgeon does no longer need to conduct an iterative procedure of re-positioning, also iterative x-ray monitoring shots can be avoided, so that the entire x-ray exposure for a patient can be reduced.

According to an aspect of the invention, there is provided a method for operating a computer-assisted surgery device comprising providing a reference structure; connecting to a first arm having a first end and a second end at the second end a main-implant in a defined geometrical orientation, wherein the first arm with the first end is connected to the reference structure; and connecting to a second arm having a first end and a second end and a plurality of segments, at the second end a sub-implant in a defined geometrical orientation with respect to an implantation trajectory of the sub-implant, wherein at least two adjacent segments are coupled with a joint being capable of being controllably brought from a fixed state into a released state and vice versa, wherein the second, segmented arm with the first end is connected to the reference structure; determining a required position and orientation of the connected sub-implant having the implantation trajectory for bringing the implantation trajectory of the sub-implant into a direction, so that the implantation trajectory of the sub-implant corresponds to a joining portion of the main-implant with the sub-implant; bringing the second arm into the released state; controlling a motion of the second arm based on the determined required motion; bringing the second arm from the released state into the fixed state; and operating the sub-implant toward the implantation trajectory of the sub-implant.

Thus, not only a tooling device can be brought into the correct position and orientation, but also a sub-implant, which cooperates with the main-implant. The sub-implant, for example, can be a locking screw, which is received in a main-implant's traverse borehole at a joining portion of the main-implant, so that the method may provide a possibility to position a sub-implant in a correct position and orientation with respect to a main-implant. As the sub-implant usually follows an implantation trajectory, the principle is similar to the tooling trajectory as described above.

According to a further aspect of the invention a method for operating a computer-assisted surgery device is provided, comprising providing a reference structure; connecting to a first arm having a first end and a second end at the second end a main-implant in a defined geometrical orientation, wherein the first arm with the first end is connected to the reference structure; connecting to a second arm having a first end and a second end at the second end a guiding device in a defined geometrical orientation with respect to a guiding trajectory of the guiding device, wherein the second arm with the first end is connected to the reference structure; identifying a main implant with a joining portion being connected to the second end of the first arm, determining a required position and orientation of the guiding device having the guiding trajectory based on a stored geometry of the identified main implant and its joining portion for bringing the guiding trajectory of the tool into a direction, so that the guiding trajectory of the guiding device corresponds to a joining portion of the main-implant with a device to be guided; controlling a motion of the second arm based on the determined required motion for bringing the guiding trajectory of the guiding device into a direction, so that the guiding trajectory of the guiding device corresponds to a joining portion of the main-implant with the guiding device; and operating the device to be guided toward the guiding trajectory.

Thus, it is possible to support the surgeon with positioning a tool relative to a main implant. The computer assisted device may provide a guiding device for guiding e.g. a drill or a K-wire. The computer assisted surgery device may operate the tool, e.g. a drill. However, in some counties it is not allowed to operate a device without human intervention during surgery. In these cases, the computer assisted surgery device may provide a guide for a drill, e.g. a sleeve which may lead the drill into the desired direction. The direction of the drilling operation is controlled by the computer assisted surgery device by positioning of the guiding device, e.g. a sleeve, whereas the forward feed is done by the surgeon manually.

According to a further aspect of the invention there is provided a method for operating a computer-assisted surgery device, comprising providing a reference structure; connecting to a first arm having a first end and a second end at the second end a main-implant in a defined geometrical orientation, wherein the first arm with the first end is connected to the reference structure; connecting to a second arm having a first end and a second end at the second end a tool in a defined geometrical orientation with respect to a tooling trajectory of the tool, wherein the second arm with the first end is connected to the reference structure; identifying a main implant with a joining portion being connected to the second end of the first arm, determining a required position and orientation of the connected tool having the tooling trajectory based on a stored geometry of the identified main implant and its joining portion for bringing the tooling trajectory of the tool into a direction, so that the tooling trajectory of the tool corresponds to a joining portion of the main-implant with the tool; controlling a motion of the second arm based on the determined required motion for bringing the tooling trajectory of the tool into a direction, so that the tooling trajectory of the tool corresponds to a joining portion of the main-implant with the tool; and operating the tool toward the tooling trajectory.

Thus, it is possible to support the surgeon with positioning a tool relative to a main implant. The computer assisted device may operate the tool. However, also the surgeon may operate the tool, but supported by the device.

According to a further aspect of the invention there is provided a method for operating a computer-assisted surgery device, comprising providing a reference structure; connecting to a first arm having a first end and a second end at the second end a main-implant in a defined geometrical orientation, wherein the first arm with the first end is connected to the reference structure; connecting to a second arm having a first end and a second end at the second end a sub-implant in a defined geometrical orientation with respect to an implantation trajectory of the sub-implant, wherein the second arm with the first end is connected to the reference structure; identifying a main implant with a joining portion being connected to the second end of the first arm, determining a required position and orientation of the connected sub-implant having the implantation trajectory based on a stored geometry of the identified main implant and its joining portion for bringing the implantation trajectory of the sub-implant into a direction, so that the implantation trajectory of the sub-implant corresponds to a joining portion of the main-implant with the sub-implant; controlling a motion of the second arm based on the determined required motion for bringing the implantation trajectory of the sub-implant into a direction, so that the implantation trajectory of the sub-implant corresponds to a joining portion of the main-implant with the sub-implant, and operating the sub-implant toward the implantation trajectory.

Thus, it is possible to support the surgeon with positioning a sub-implant, e.g. a locking screw or a traverse nail relative to a main implant. The computer assisted device may position the sub-implant. However, also the surgeon may position the sub-implant, but supported by the device, e.g. by instruction the surgeon what to do, e.g. to move the sub-implant into a certain direction for a predetermined direction.

According to an embodiment of the invention identifying comprises entering a main implant identifier via a human interface allowing identification of the main implant with its joining portion and its corresponding geometry from a database.

Thus, an identification option may be provided, which provides the surgeon the option to enter or identify a particular geometry of an implant, which may be input by entering an identifier. The device may receive the corresponding geometry data from a local or remote database, e.g. via a network connection. The identification may take place by entering a code representing the implant to be identified.

According to an embodiment of the invention, identifying comprises receiving imaging data of a connected main implant, and image recognizing and identifying based thereon the connected main implant with its joining portion and its corresponding geometry from a database.

Thus, the identification may be supported by image recognition, where particular imaged geometries are recognized from an e.g. x-ray image and then allocated to a particular geometry information or further information of the recognized item. The recognized item may be a main implant, a sub-implant, a bone, a tool, a K-wire or a guiding device. Recognition may be supported by a reference geometry which may include fiducial markers having a unique spatial projection, which allows determining the orientation and position of the item on a single image, e.g. an x-ray image.

According to an embodiment of the invention the method for operating device for computer-assisted surgery further comprises determining a spatial deviation of a present relative position of the guiding device and the device to be guided by the guiding device, and a spatial deviation of an intended relative position of the guiding device and the device to be guided by the guiding device, based on reference geometries provided with the guiding device and the device to be guided.

Thus, it is possible to recognize reference geometries of the used devices, i.e. the guiding device and the guided device, for example a reference geometry of a sleeve and a reference geometry of a drill. By recognizing reference geometries, e.g. in an x-ray image, the spatial position of e.g. a sleeve and a drill can be determined, so that it can be determined how far a drill has entered the location. Not only the spatial position between the sleeve and the drill with respect to each other can be determined, but also between the drill and the main implant. Instead of the drill, also the position of a K-wire may be recognized and determined accordingly. Thus, it can be avoided to drive the drill or K-wire too far into the bone.

According to an embodiment of the invention the method for operating a device for computer-assisted surgery further comprises bringing the second arm having a plurality of segments with at least two adjacent segments being coupled with a joint and being capable of being controllably brought from a fixed state into a released state and vice versa, into the released state before controlling a motion of the second arm based on the determined required motion; and bringing the second arm from the released state into the fixed state before operating the tool and the sub-implant, respectively, toward the tooling trajectory and the implantation trajectory, respectively.

According to an embodiment of the invention, the method further comprises sensing positional information of the first arm and the second arm at their connecting joints between respective segments and between the first and second arm and their respective reference structure and determining a relative position of the second end of the first arm and the second end of the second arm.

Thus, the sensing information on each of the joints with respect to the position and orientation of adjacent segments in combination may be used to determine the relative position and orientation of the second end of the first arm and the second end of the second arm. As the main-implant usually is connected to the second end of the first arm in a fixed manner, and also the sub-implant or the tooling device is connected to the second end of the second arm in a fixed manner, the combination of the sensing information may be used to determine the relative position and orientation of the main-implant and the sub-implant or the main-implant and the tool.

According to an embodiment of the invention, the method further comprises determining a spatial position of a reference geometry connected to the second end of the first arm and a reference geometry connected to the second end of the second arm by analyzing an x-ray image including the reference geometry connected to the second end of the first arm and the reference geometry connected to the second end of the second arm, determining a relative spatial position of the second end of the first arm and the second end of the second arm with respect to each other, and comparing the determined relative spatial position with the relative position determined based on the sensed positional information at the connection joints and the reference structure.

Thus, by providing a relative position and orientation of the second end of the first arm and the second end of the second arm by two different ways, a full redundancy of the determination of the relative position and orientation can be achieved. As both ways to determine the spatial position and orientation, by sensing data of the joints on the one hand and by a resulting x-ray image on the other hand, are fully independent of each other, a full redundancy is given.

According to an embodiment of the invention, the method further comprises identifying the connected main-implant with respect to its geometry, and determining a required position and orientation of the connected tool and sub-implant, respectively, based on the identified geometry of the main-implant.

Thus, a full match between the main-implant and the used tool or the used sub-implant can be achieved and the method may provide a monitoring, whether the tool and the main-implant or the sub-implant and the main-implant match to each other. The information with respect to the main-implant, the tool and the sub-implant may be taken from a database having stored therein geometrical data with respect to the main-implant, the used tool and the intended sub-implant.

It should be noted, that the method may also be applied to a virtual system, where a surgeon may train the entire process in a virtual reality. In this case, either a real main-implant, a real tool or a real sub-implant may be used, but the human body may be virtually displayed in a virtual reality, or even the main-implant, the tool and the sub-implant may be provided as a virtual illustration. The virtual illustration of the human body and also of the main-implant, the tool and the sub-implant may be merged to a real image of the computer-assisted surgery device, in particular the first and second arm, so that the surgeon may see the real computer-assisted surgery device but a virtual main-implant, a virtual tool, and a virtual sub-implant in a virtual patient environment.

BRIEF DESCRIPTION OF THE FIGURES

Exemplary embodiments will be described in more detail with respect to the enclosed figures, where same or corresponding references refer to the same or corresponding elements and structures.

DETAILED DESCRIPTION OF EXEMPLARY EMBODIMENTS

Figure 1:
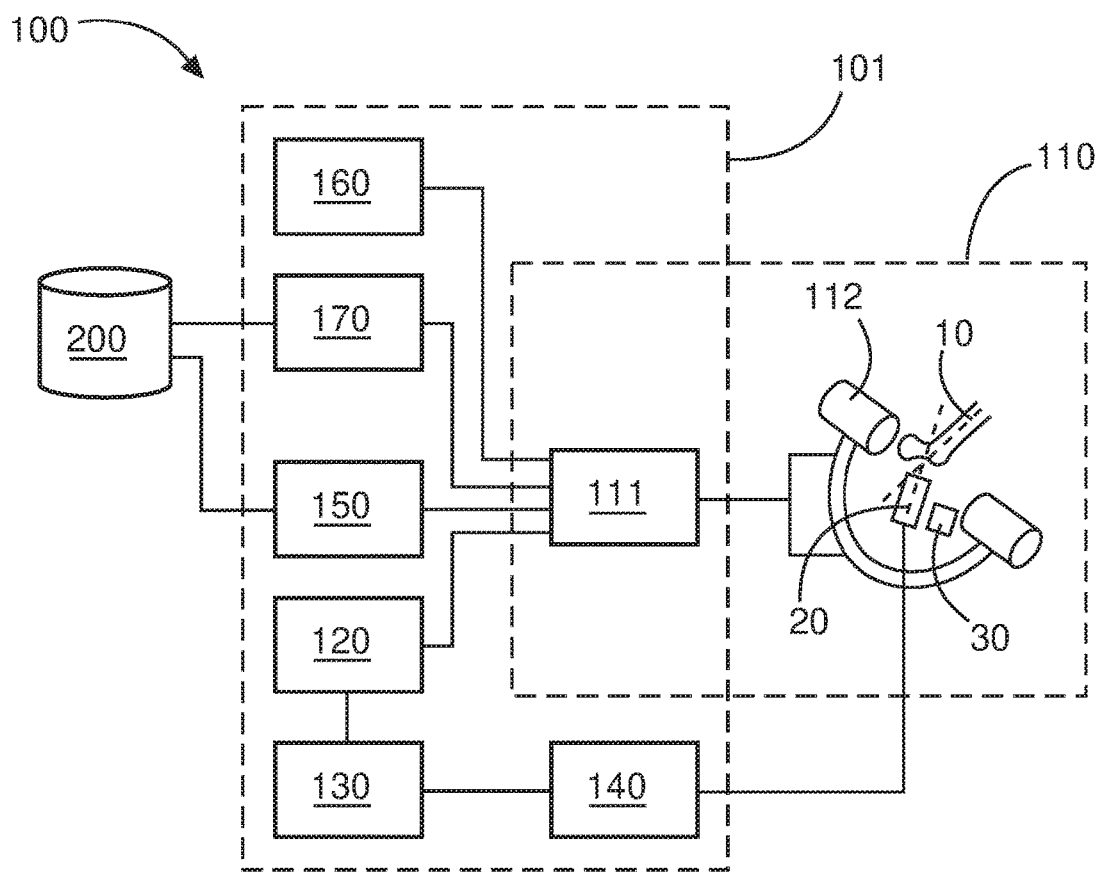
FIG. 1 illustrates a schematic overview on a device for computer-assisted surgery according to an exemplary embodiment of the invention.

The present invention provides a computer-assisted surgery system and method for operating the same that allows an easier positioning of implants and sub-implants with respect to bony structures. This device and method for operating the same also allows a support in positioning implants and sub-implants, as well as implants and tooling devices with respect to each other. The invention overcomes problems with pin and screw targeting, that in multiple indications requires significant radiation, and in some cases requires multiple passes with a K-wire and further has a limited accuracy in case 3D information on the pin or screw position is normally not available in the operational room. As in the past, often iterative and free-hand targeting with fluoroscopy was applied, for some applications combined with temporary K-wires to verify position or a full navigation with bone trackers and a stereo camera, the drawbacks of such methods and devices can be overcome with the present invention.

The present invention provides a device and a method for operating the device which constitutes a combination of a stereotactic method with a robotic arm arrangement for multiple targeting exercises in traumatology. The concept is to identify the relative spatial position of bony and anatomical structures to e.g. a main-implant, e.g. a sleeve held by a first robotic arm and a sub-implant, e.g. a locking screw held by a second robotic arm, by stereotactic imaging, which stereotactic imaging may be a fluoroscopy imaging or an ultrasound imaging. The targeting sleeve or targeting device itself or a rigidly connected structure may serve as reference between single or multiple C-arm views. With the assumption that the position of the bony structure is relatively stable, movements of the targeting device can then be displayed live relative to the bony structures by simply feeding in the relative position information from a robotic arm, without the need for further imaging. That means, that a targeting task for example for a pin or screw placement can be accurately performed in simple steps. These steps may for example include acquiring bi- or multi-planar images of the relevant bony structure with a reference body, which may be attached to the robotic arm, and positioning by a surgeon a targeting sleeve or targeting device connected to the robot to be aligned with the desired pin or screw trajectory while the relative position is displayed on a screen by the arm movement information coming from position sensors in the robot and the assumption that the bony fragment stays stationary during the process. Then, a verification can be performed that the relative position of targeting device and anatomical structure is now correct through additional imaging.

Robotic arm in this context means a mechanical arm with at least 5 degrees of freedom DoF for the end effector, which may be the targeting device, where relative movements of the tip can be tracked through position sensors in all relevant moving parts and hinges. The hinges or joints of the robotic arm could also be equipped with actuators and/or clutches in order to constrain movements in certain direction and/or block the device position during control imaging.

Stereotactic imaging is calculating the position and orientation of a three-dimensional representation of an anatomic structure by correlating, for example, two fluoroscopic images with a relative angle between them. Since the relative position and orientation by standard C-arms is typically not tracked or known, the invention may utilize a stationary reference body with, for example, radio-dense markers that are visible in both images. In the targeting application for the femoral head, the femoral head is assumed as spherical. So in this particular case, no underlying CT scan is needed to display the position of a screw relative to the head in the three-dimensional image. For application in more general structures, a three-dimensional shape estimation may be provided with assumptions about the bone shape by comparing the same with a bone database. For a more accurate registration of three-dimensional structures, a pre- or intra-operative CT scan may be fed in as underlying information, and by identifying the outer contour of structures or fragments and comparing them to the object shape known from the three dimensional scan, the position and orientation may be identified. This may be facilitated by replacing a reference body in the field of view for images. In the approach, this reference body may be connected to the robotic arm or be integrated in the arm.

Thus, the invention provides a highly accurate reproducible process and a device which may provide a highly accurate and reproducible process to target pins or screws. Especially, if there is an underlying CT, the position of any screw or pin or implant can be accurately planned and executed by the surgeon in the surgery while significantly reducing the need for radiation and potentially increasing speed of surgery.

For this purpose, the following exemplary embodiments are described along the figures to illustrate the operation of the device for computer-assisted surgery and the method for operating the same.

FIG. 1 illustrates a device for computer-assisted surgery 100 and the schematic structure thereof. The device for computer-assisted surgery 100 may have a processing unit 101 and a field unit for example in form of an imaging device 112, which may be a C-arm x-ray imaging device. The processing unit may have access to a database 200, in particular a bone database 200. The entire operation situation, here illustrated as a bony structure 10 of a patient 1, a targeting device for an implant 20 and a targeting device for a sub-implant 30 can be imaged by an imaging device 112. It should be noted that for positioning of a single part implant only the targeting device 20 for a single implant is required. In case not only a single implant, but a multiple part implant is to be applied, e.g. a femoral nail and its locking screw, not only a single implant targeting device is required, but an implant targeting device 20 for a main-implant, e.g. the femoral nail, and an implant targeting device 30 for a sub-implant, e.g. its locking screw, are required. It should also be noted, that of course a here not illustrated implant 28 may be connected to the implant targeting device 20. If required, also a here not illustrated sub-implant 38 may be connected to the sub-implant targeting device 30.

An image of the implanting situation, which is taken by the imaging device 112 may be transferred to the processing unit 101. In case that the imaging device 112 acquires more than one image, in particular more than one image from different points of view, the different images may be provided to the processing unit 101. In case a plurality of images are acquired, in particular from different points of view, a correlation unit 111 may correlate the different images, in order to, for example, combine two or more bi-planar images to a three-dimensional illustration of the implanting situation. This image information may then be provided to different units of the processing unit 101. The processing unit 101 may determine based on the acquired imaging information acquired by the image acquiring unit 110 a deviation of an implant trajectory of a sub-implant 38 to be implanted or a tooling trajectory 45 of a tool 48 and a joining portion 29 of a main-implant 28 to which the sub-implant 38 should be positioned or e.g. a drill hole drilled by the tool 48 should match. This deviation may be determined and acquired by the deviation acquiring unit 120. The processing unit 101 may use a determined position, which may be determined by the position determining unit 160 based on the acquired images. The processing unit may also receive supporting information, for example received from an implanting area determining unit 150 and an identification unit 170 for identifying a type of an implant, a type of sub-implant or a type of tool. The implanting area determining unit 150 and the identification unit 170 for a type of an implant, sub-implant or tool may receive information for determining the implanting area and the identification of a type of an implant, sub-implant or tool from an external database 200. The external database 200 may have included information regarding anatomical geometries. This information regarding anatomical geometries may have included a statistical bone database where empirical information of different bone geometries are stored, but may also include individual patient related bone data, acquired before.

Figure 5:
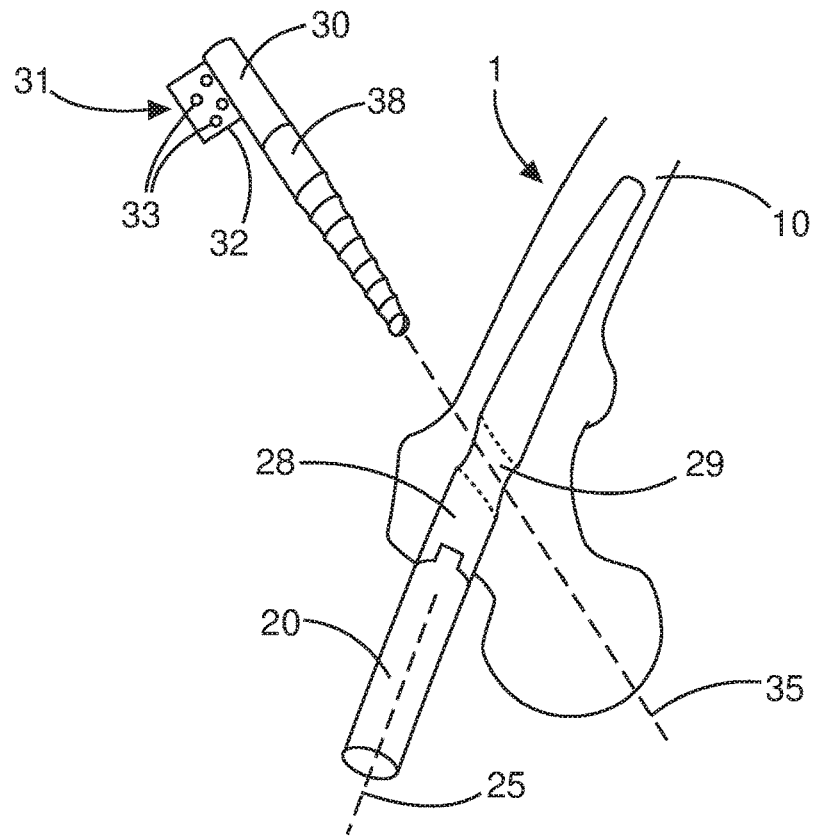
FIG. 5 illustrates a main-implant connected to a main-implant targeting device and a sub-implant connected to a sub-implant targeting device having attached thereto a reference geometry according to an exemplary embodiment of the invention.

The deviation acquiring unit 120 may acquire a deviation from the main-implant implanting trajectory of the main-implant targeting device and/or main-implant and the implanting trajectory of a joining portion or a tooling trajectory of a tool. Based thereon, the motion determining unit 130 may determine the required motion. The motion determining unit 130 provides this information to a motion controlling unit 140, which in turn may control the motion of for example a robot arm (which is not illustrated here) to bring the implantation trajectory 35 related to a sub-implant targeting device 30 or sub-implant 38 (or alternatively the tooling trajectory 45 related to a tooling device 40 or tool 48) into an alignment with a joining portion 29 of a main-implant, as illustrated in FIG. 5.

Figures 2, 3, 4:
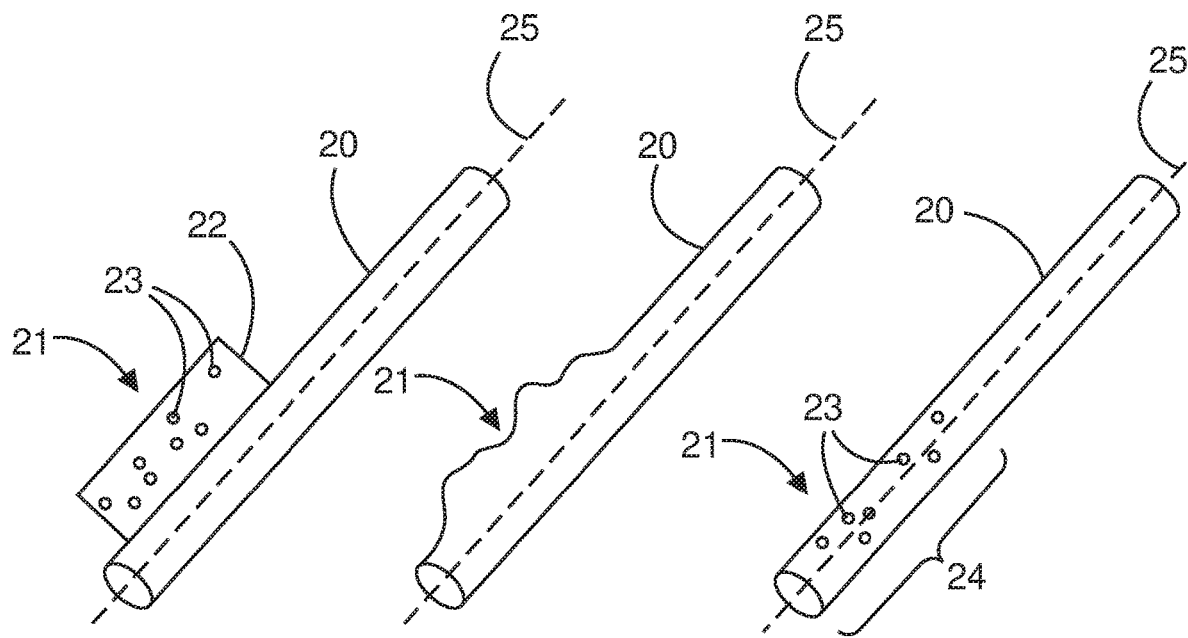
FIG. 2 illustrates an implant targeting device having attached thereto a reference geometry with fiducial markers according to an exemplary embodiment of the invention.
FIG. 3 illustrates an implant targeting device having a reference geometry in form of a unique projection geometry according to an exemplary embodiment of the invention.
FIG. 4 illustrates an implant targeting device having a reference geometry in form of an included plurality of fiducial markers according to an exemplary embodiment of the invention.

FIG. 2 illustrates an implant targeting device 20 with a reference geometry 21 according to an embodiment of the invention. In order to simplify the determination of the geometrical position and orientation of an implant targeting device 20 and its trajectory 25, a reference body 22 may be provided, which may be attached to the implant targeting device 20. The reference body 22 may also be provided with fiducial markers 23. It should be noted, that instead of the implant targeting device 20, the reference body 22 may also be attached to the implant 28 (not illustrated), which is to be connected to the implant targeting device 20. However, it should be noted, that the position of an implant 28 which is to be connected to the implant targeting device 20 is fixed and defined with respect to position and orientation, so that attaching the reference body 22 to the implant targeting device 20 may also allow the determination of the position and orientation of the implant 28 which is to be connected to the implant targeting device 20, without having the reference body 22 too close to the bony structure 10. This also applies for the position and orientation of the joining portion 29 of a main-implant to which a sub-implant 38 or a tool 48 may be joined.

FIG. 3 illustrates an implant targeting device 20 with a reference geometry 21 according to another embodiment of the invention. As an alternative or in addition to the embodiment illustrated with respect to FIG. 2, the implant targeting device 20 may also have as a reference geometry a unique shape, which shape allows an identification of the position and orientation of the implant targeting device 20 in an x-ray image. FIG. 3 illustrates this by a schematic unique shape of the implant targeting device 20. However, this may require a sufficient contrast of the implant targeting device over the environment in an x-ray image.

FIG. 4 illustrates an implant targeting device 20 with a reference geometry 21 according to yet another embodiment of the invention. As a further alternative, fiducial markers 23 may be provided in a unique pattern directly within the implant targeting device 20 in order to achieve the same purpose as illustrated in the embodiment of FIG. 2. It should be noted, that the unique distribution and pattern of fiducial markers 23 may also be provided directly into the implant 28 which is to be connected to the implant targeting device 20, as the internal fiducial markers 23 when being located within the implant shape may avoid any disturbance when implanting the implant 28 into an implanting area of a bony structure. Thus, the integrated reference geometry 24 may be provided as an integral portion of the implant targeting device and as an alternative may also be provided as an integral portion of the implant itself. If providing a reference geometry, e.g. in form of fiducial markers to both, the implant targeting device 20 and the implant 28, also the correct positioning of the implant 28 onto the targeting device 20 may be determined and monitored. This also applies for position and orientation of the joining portion 29 of a main-implant to which a sub-implant 38 or a tool 48 may be joined. Corresponding reference geometries at the sub-implant targeting device 30, the sub-implant 38, the tooling device 40 and/or the tool 48 may be used to bring them into an alignment with the joining portion 29, as well to monitor whether the sub-implant 38 is in the correct position with respect to the sub-implant targeting device 30, or whether the tool 48 is in the correct position with respect to the tooling device 40.

FIG. 5 illustrates the positioning of a sub-implant 38 with respect to a main-implant 28. Usually, at first the main-implant 28 is implanted to a bony structure 10 of a patient 1, and then the sub-implant 38 is implanted to the bony structure 10 of the patient 1 and brought into a desired alignment with the main-implant 28. The main-implant 28 is usually connected to the main-implant targeting device 20, which then may be connected to a robot arm of a computer-assisted surgery device. In the same manner, the implant 38 may be connected to a sub-implant targeting device 30, which may be connected to a second arm of a computer-assisted surgery device. In the same manner as illustrated in FIGS. 2, 3 and 4, also the sub-implant targeting device 30 may be provided with a reference body 32, which also may have fiducial markers 33 for identifying the position and orientation of the sub-implant targeting device 30 and thus of the sub-implant 38 in an x-ray image. Thus, a reference geometry 31 for a sub-implant targeting device 30 may be provided. It should be understood, that in the same manner as it is described with respect to FIGS. 2, 3 and 4, the reference geometry 31 may also integrally be formed to the sub-implant targeting device 30, for example in form of integrally positioned fiducial markers 33. Although the relative position of the main-implant targeting device 20 and the sub-implant targeting device 30 may be determined based on sensed position and orientation information on the joints 184, 194 of the robot arms 180, 190, a reference geometry 21 of the main-implant targeting device 20, not illustrated here, and a reference geometry 31 of the sub-implant targeting device 30 may allow a determination of the position and orientation of the main-implant targeting device 20 and the sub-implant targeting device 30, and consequently of the main-implant 28 and the sub-implant 38 with respect to each other. Thus, it is possible that the sub-implant 38 may be brought into a correct orientation, so that the implanting trajectory 35 of the sub-implant targeting device 30 meets the joining portion 29 of the main-implant 28.

Figure 6:
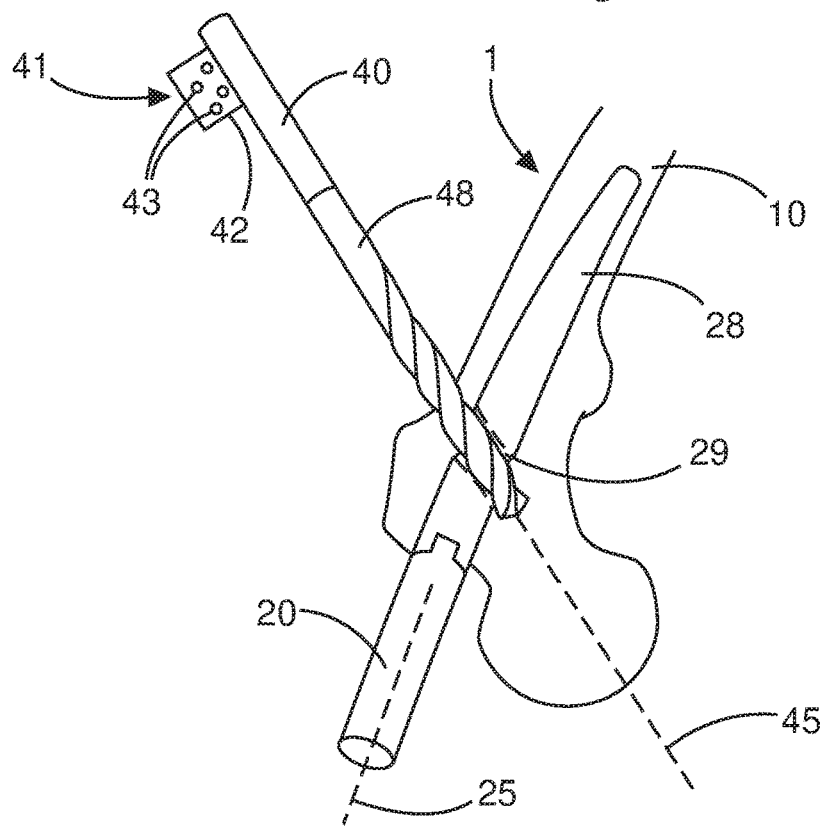
FIG. 6 illustrates an already implanted main-implant connected to a main-implant targeting device and a tool connected to a tooling device having attached thereto a reference geometry according to an exemplary embodiment of the invention.

FIG. 6 illustrates, in correspondence with FIG. 5, the positioning of a tool 48 with respect to a main-implant 28. The main-implant 28 is usually connected to an implant targeting device 20, which then may be connected to a robot arm of a computer-assisted surgery device. In the same manner, the tool 48, e.g. a drill, may be connected to a tooling device 40, e.g. a rotary drive, which may be connected to a second arm 190 of a computer-assisted surgery device. In the same manner as illustrated in FIGS. 2, 3 and 4, also the tooling device 40 may be provided with a reference body 42, which also may have fiducial markers 43 for identifying the position and orientation of the tooling device 40 and thus of the tool 48 in an x-ray image.

Thus, a reference geometry 41 for a tooling device 40 may be provided. It should be understood, that in the same manner as it is described with respect to FIGS. 2, 3 and 4, the reference geometry 41 may also integrally be formed in the tooling device 40, for example in form of integrally positioned fiducial markers 43. Although the relative position of the main-implant targeting device 20 and the tooling device 40 may be determined based on sensed position and orientation information on the joints 184, 194 of the robot arms 180, 190, a reference geometry 21 of the main-implant targeting device 20, not illustrated here, and a reference geometry 41 of the tooling device 40 allows a determination of the position and orientation of the main-implant targeting device 20 and the tooling device 40, and consequently of the main-implant 28 and the tool 48 with respect to each other. Thus, it is possible that the tool 48 may be brought into a correct orientation, so that the tooling trajectory 45 of the tooling device 40 meets the joining portion 29 of the main-implant 28.

Figures 7, 8, 9:
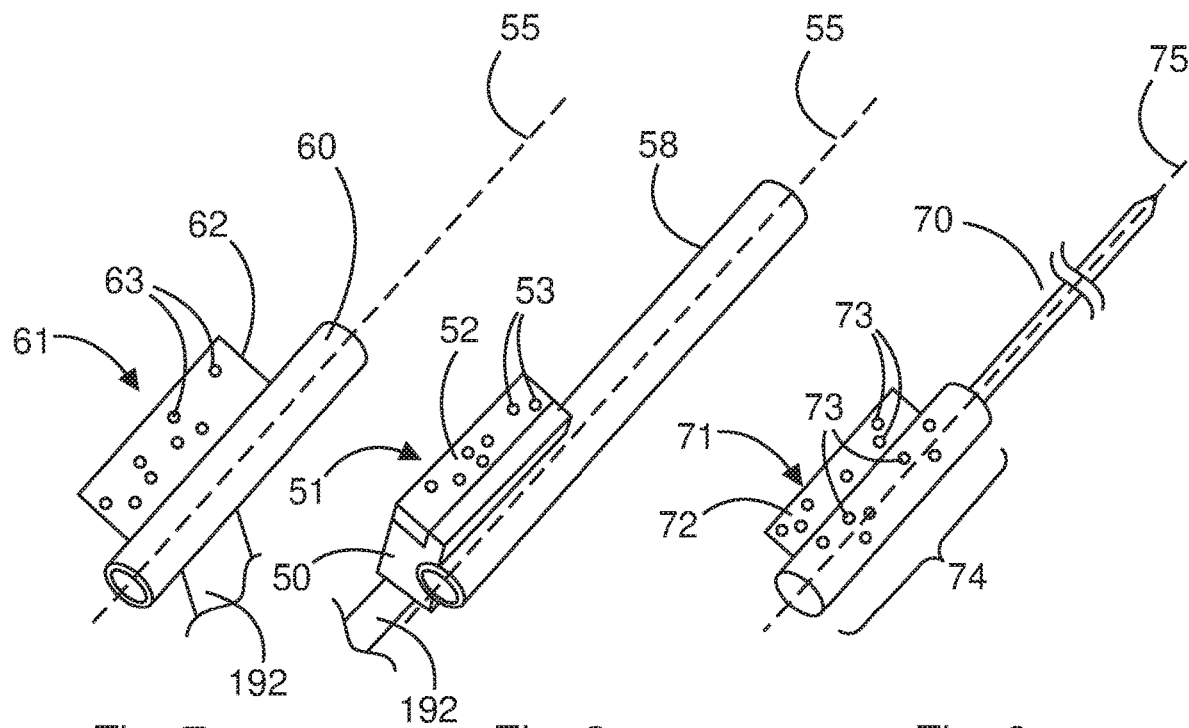
FIG. 7 illustrates a targeting sleeve or tool/K-wire guiding device having attached thereto a reference geometry with fiducial markers according to an exemplary embodiment of the invention.
FIG. 8 illustrates a sleeve receptacle with a connected/received sleeve, the sleeve receptacle having a reference geometry with fiducial markers according to an exemplary embodiment of the invention.
FIG. 9 illustrates a K-wire having a reference geometry in form of an incorporated plurality of fiducial markers in addition or as alternative to a reference body with fiducial markers according to an exemplary embodiment of the invention.
Figure 10:
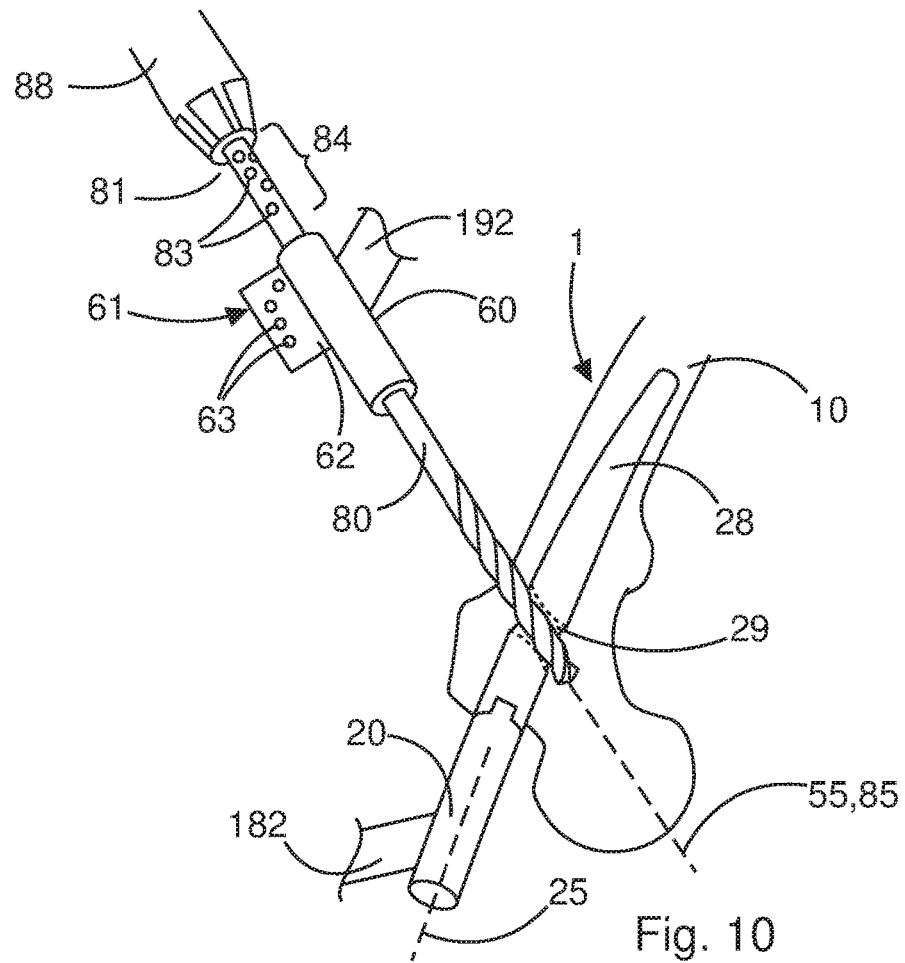
FIG. 10 illustrates a main-implant connected to a main-implant targeting device and a drill having a reference geometry which drill is guided by a sleeve having attached thereto a reference geometry according to an exemplary embodiment of the invention.
Figure 12:
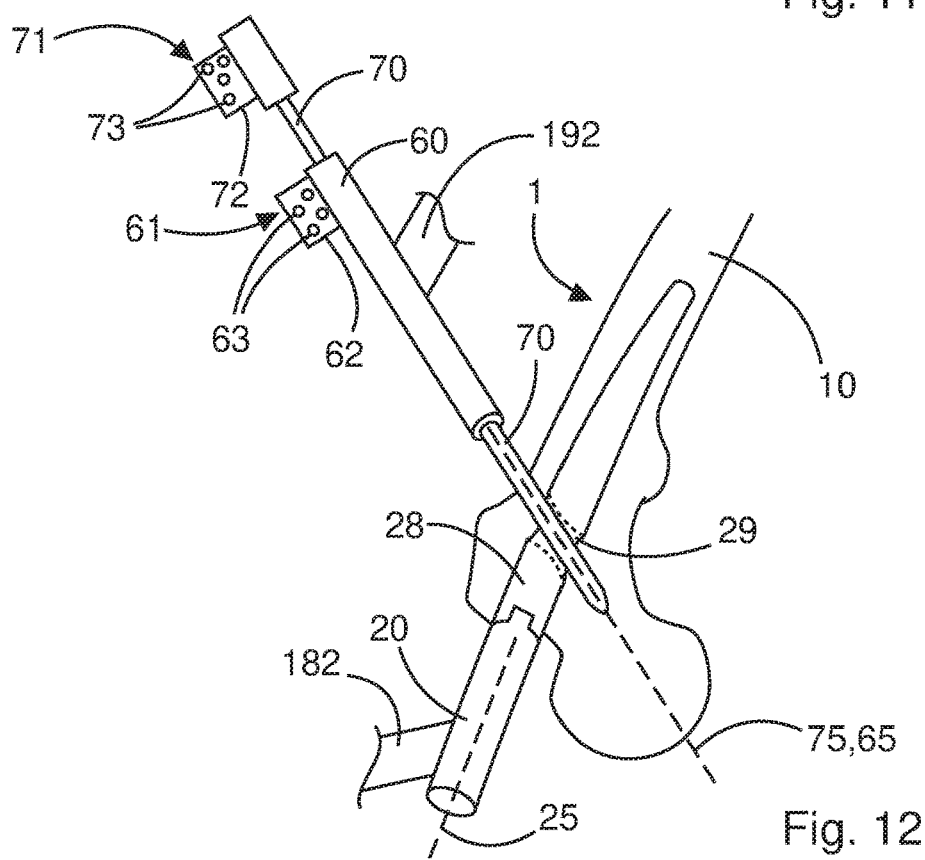
FIG. 12 illustrates an already implanted main-implant connected to a main-implant targeting device and a K-wire having a reference geometry in form of a reference body with fiducial markers, the K-wire being guided by a K-wire guiding device having attached thereto a reference geometry with fiducial markers according to an exemplary embodiment of the invention.

FIG. 7 illustrates a guiding device, e.g. in form of a targeting sleeve 60. The sleeve 60 may be used to guide a tool, e.g. a drill 80, as illustrated in FIG. 10. The sleeve 60 may also be used to guide a K-wire 70, as it is illustrated in FIG. 12. The sleeve 60 has a through bore, which may guide e.g. a drill 80. The through hole may define a guiding direction as a guiding trajectory 55. The sleeve 60 may have a reference geometry 61. The reference geometry 61 may be designed in form of a reference body 62 being attached to the sleeve. As an alternative, the reference geometry 61 may be integrally formed with the sleeve, which is here not illustrated. It should be noted that both can be provided, an integrally formed reference geometry 61 as well as an attached reference geometry in form of a reference body 62. The reference geometry 61, regardless whether it is integrally formed or attached, may have a plurality of fiducial markers 63 together forming a unique spatial projection, which may allow determining the spatial position and orientation from a single 2-dimensional x-ray image. The sleeve may be fixedly or releasably coupled to a second end 192 of a robot arm.

FIG. 8 illustrates a sleeve receptacle 50 with a connected/received sleeve 58, the sleeve receptacle 50 has a reference geometry 51 with fiducial markers 53. The sleeve receptacle 50 may be used to receive a sleeve 58 as a guiding tool, e.g. for guiding a drill 80, as illustrated in FIG. 10. The sleeve 58 may be fixedly or releasably coupled to the sleeve receptacle 50. The sleeve 58 has a through bore, which may guide e.g. a drill 80 or a K-wire 70. The through hole may define a guiding direction as a guiding trajectory 65. The sleeve receptacle 50 may have a reference geometry 51. The reference geometry 51 may be designed in form of a reference body 52 being attached to the sleeve receptacle 50.

As an alternative, the reference geometry 51 may be integrally formed with the sleeve receptacle 50, which is here not illustrated. It should be noted that both can be provided, an integrally formed reference geometry 51 as well as an attached reference geometry in form of a reference body 52. The reference geometry 51, regardless whether it is integrally formed or attached, may have a plurality of fiducial markers 53 together forming a unique spatial projection, which may allow determining the spatial position and orientation from a single 2-dimensional x-ray image. Also the sleeve 58 may have a plurality of fiducial markers together forming a unique spatial projection, which may allow determining the spatial position and orientation from a single 2-dimensional x-ray image. The both reference geometries, the one allocated to the sleeve receptacle 50 and the one allocated to the sleeve 58, may be used to check whether the correct sleeve 58 is coupled to the receptacle 50. The sleeve receptacle may be fixedly or releasably coupled to a second end 192 of a robot arm.

FIG. 9 illustrates a K-wire having a reference geometry 71 in form of an included plurality of integrally formed fiducial markers 73 in an integral portion 74 of the K-wire, in addition or as alternative to a reference body 72 with fiducial markers 73 according to an exemplary embodiment of the invention. The K-wire may me manually operated by a surgeon or may be coupled to a robot arm so that the surgeon does not have to act himself.

FIG. 10 illustrates a main-implant 28 connected to a main-implant targeting device 20 and a drill 80 having a reference geometry 81 which drill 80 is guided by a sleeve 60 having attached thereto also a reference geometry 61. The drill 80 may be operated by the computer assisted surgery device or, if this does not comply with the national regulations for medical devices and surgery, may be operated by a surgeon. In the latter case the surgeon may operate a manually guided drill drive 88, which may have coupled thereto the drill 80.

The sleeve 60 provides the predetermined direction, whereas the surgeon determines the forward speed and way. Reference geometries 61, 81 at the sleeve 60 and the drill 80 may be used as references for determining e.g. whether a correct drill 80 was used with the sleeve 60, e.g. having corresponding diameters of the bore hole in the sleeve 60 and the drill 80 to avoid inclination between the drill trajectory 85 and the guiding trajectory 55 of the sleeve 60. The sleeve 60 may guide the drill 80 so that the drill 80 meets the joining portion 29 of the main implant. Further the reference geometries 61 and 81 may be used to determine how far a drill has entered the sleeve 60 for avoiding that a drill 80 enters too far into the bone 10. The sleeve 60 may be connected to a second end 192 of a robot arm.

Figure 11:
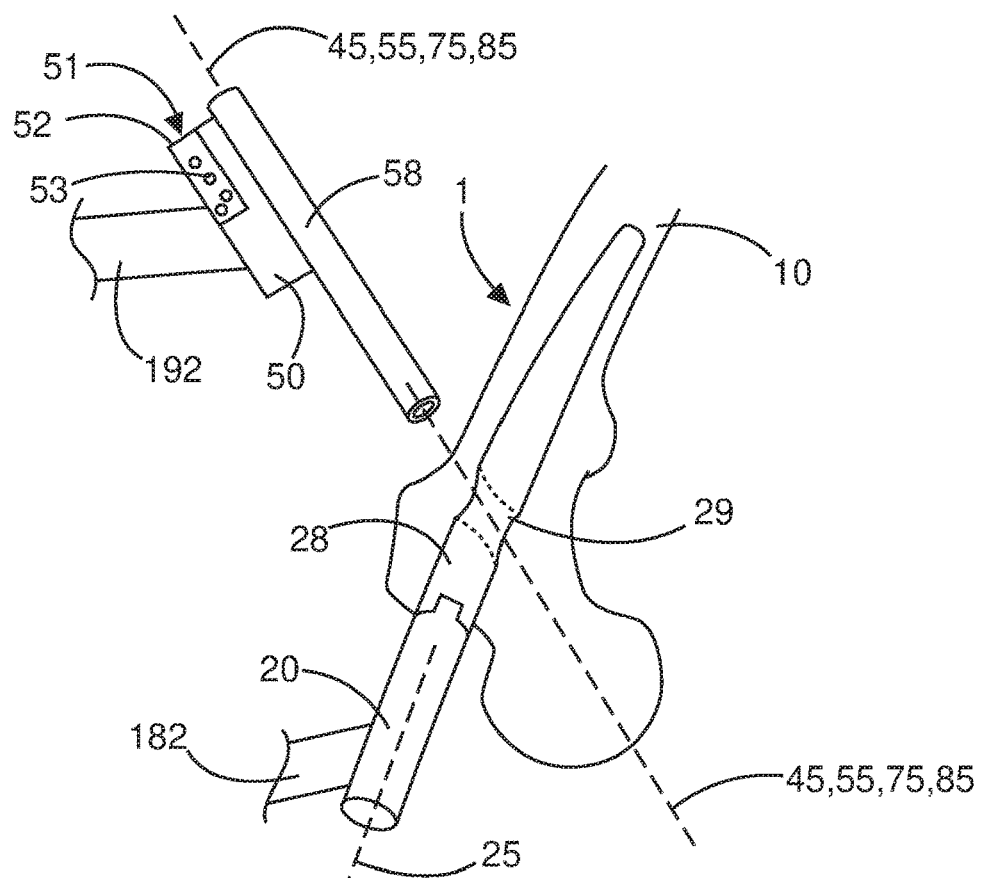
FIG. 11 illustrates a main-implant connected to a main-implant targeting device and a sleeve receptacle with a connected/received sleeve, the sleeve receptacle having a reference geometry with fiducial markers according to an exemplary embodiment of the invention.

FIG. 11 illustrates a main-implant 28 connected to a main-implant targeting device 20 and a sleeve receptacle 50 with a connected/received sleeve 58. The sleeve receptacle 50 has a reference geometry 51 with fiducial markers 53. The sleeve receptacle may be connected to a second end 192 of a robot arm. The sleeve may be exchanged, depending on the device to be guided. The correct coupling between a sleeve 58 and the receptacle 50 may be established by an additional reference geometry on the sleeve side, which is not illustrated here. Thus, a correct selection and coupling of a sleeve 58 with the corresponding sleeve receptacle may be carried out. The sleeve 58 having a guiding trajectory 55 may guide a tool (not illustrated) with a tooling trajectory 45, which then is coincident with a guiding trajectory 55 of the sleeve 58. In the same way, the sleeve may guide a drill with a drilling trajectory 85 or a K-wire with a tooling trajectory 75. The sleeve 60 provides the predetermined direction, whereas the surgeon may determine the forward speed and way. The sleeve 60 may guide the drill 80 (not illustrated here) or a K-wire (also not illustrated here) so that the drill meets the joining portion 29 of the main implant. Further, the reference geometries 51 on the sleeve receptacle 50 and at a drill or K-wire may be used to determine how far a drill or K-wire has entered the sleeve 60 for avoiding that a drill or K-wire enters too far into the bone 10. The sleeve receptacle 50 may be connected to a second end 192 of a robot arm.

FIG. 12 illustrates an already implanted main-implant 28 connected to a main-implant targeting device 20 and a K-wire 70 having a reference geometry 71 in form of a reference body 72 with fiducial markers 73. The K-wire 70 being guided by a K-wire guiding device, here a sleeve 60, having attached thereto a reference geometry 61 with fiducial markers 63. The K-wire 70 may be operated by the computer assisted surgery device or, if this does not comply with the national regulations for medical devices and surgery, may be operated by a surgeon. In the latter case the surgeon may operate a manually guided K-wire 70. The sleeve 60 provides the predetermined direction, whereas the surgeon determines the forward speed and way. Reference geometries 71, 81 at the sleeve 60 and the K-wire 70 may be used as references for determining e.g. whether a correct K-wire 70 was used with the sleeve 60, e.g. having corresponding diameters of the bore hole in the sleeve 60 and the K-wire 70 to avoid undue inclination between the tooling trajectory 75 of the K-wire and the guiding trajectory 65 of the sleeve 60. The sleeve 60 may guide the K-wire 70 so that the K-wire 70 meets the joining portion 29 of the main implant. Further, the reference geometries 61 and 71 may be used to determine how far a K-wire 70 has entered the sleeve 60 for avoiding that a K-wire 70 enters too far into the bone 10. The sleeve 60 may be connected to a second end 192 of a robot arm.

Figure 13:
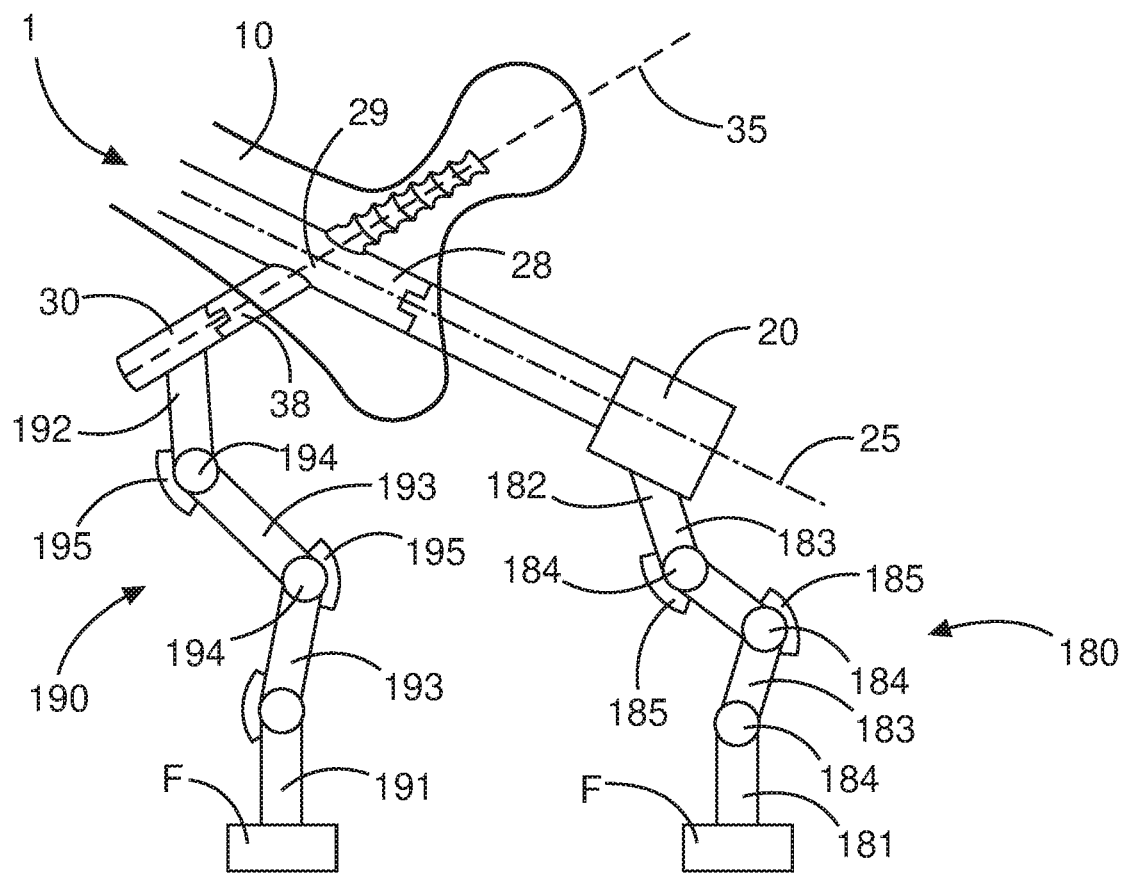
FIG. 13 illustrates a device for computer-assisted surgery according to an exemplary embodiment of the invention, having a first arm for positioning of a main-implant and a second arm for positioning a sub-implant according to an exemplary embodiment of the invention.

FIG. 13 illustrates the situation of FIG. 5, where the sub-implant targeting device 30 is connected to a second robot arm 190 and the main-implant targeting device 20 is connected to a first robot arm 180. As can be seen, as both robot arms 180 and 190 are connected to a reference structure F, the relative position of the main-implant targeting device 20 and the sub-implant targeting device 30 can be determined, in order to bring the sub-implant trajectory 35 into alignment with the joining portion 29 of the main-implant 28. The first robot arm 180 has a first end 181 connected to a reference structure F and a second end 182 to which a targeting device or an implant can be connected. The first robot arm between the first end 181 and the second end 182 has a plurality of segments 183 which are connected via joints 184. The segments 183 may be moved along their connecting joints 184 by actuators 185. The second robot arm 190 has a first end 191 connected to a reference structure F and a second end 192 to which a targeting device or an implant can be connected. The second robot arm between the first end 191 and the second end 192 has a plurality of segments 193 which are connected via joints 194. The segments 193 may be moved along their connecting joints 194 by actuators 195. The joints may be brought from a fixed state into a released state and vice versa. In a fixed state, the entire situation may be illustrated by an x-ray image in order to avoid any movement during image acquisition. After the device for computer-assisted surgery has determined the deviation of the respective trajectories and after determination of the required motion and controlling the motion to bring the trajectories into alignment, the joints may be brought from a released state into a fixed state again. It should be noted, that at first, for example, the main-implant targeting device 20 may be brought into the correct implanting position and orientation and the joints 184 may be brought from the released state into the fixed state in order to stabilize the main-implant targeting device 20 in its intended position, and therefore to fix the position of the implant 28 with respect to the bony structure 10, and afterwards, the positioning of the sub-implant may take place. In this case, after the joints 184 of the first arm 180 are brought into a fixed state, positioning of the second arm 190 takes place in order to bring the sub-implant 38 into the correct position with respect to the main-implant 28. It should be noted, that instead of the sub-implant and sub-implant targeting device 30, also a tooling or other device may be coupled to the second arm 190, in order to drill a hole into the bony structure 10 which is in alignment with the joint 29 of the main-implant 28.

What is described with respect to FIG. 13 in view of the sub-implant 38 and its alignment with the joining portion 29 of the main-implant 28 as illustrated in FIG. 5, in the same way applies to the tool 48 and its alignment with the joining portion 29 of the main-implant 28 as illustrated in FIG. 6.

Accordingly, what is described with respect to FIG. 13 also applies to the guiding sleeve 58, 60, K-wire 70, drill 80, as illustrated in FIGS. 10, 11 and 12.

Figure 14:
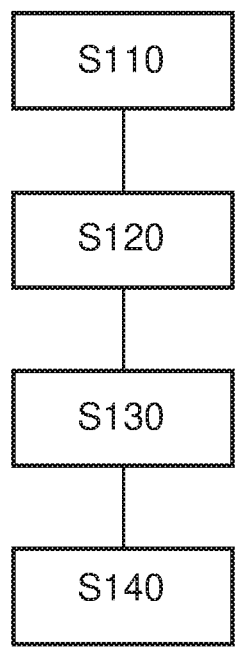
FIG. 14 illustrates a schematic sequence of procedural steps of a method for operating a computer-assisted surgery device according to an exemplary embodiment of the invention.

FIG. 14 illustrates the method steps of the method for operating the computer-assisted surgery system. The method generally includes acquiring an image, e.g. a three-dimensional image S110 and based thereon acquiring a deviation of an implanting trajectory 35 of a sub-implant targeting device 30 or sub-implant 38 from an alignment with a joining portion 29 of a main-implant 28, S120. After having acquired a deviation of the implanting trajectory 35 from an alignment, the method proceeds with determining a measure of a required motion S130 and then with controlling a motion of a sub-implant targeting device S140. Controlling the motion may be achieved by either driving actuators 185, 195 of the device for computer-assisted surgery, or by providing instructions to the surgeon how to move the device for computer-assisted surgery.

Figure 15:
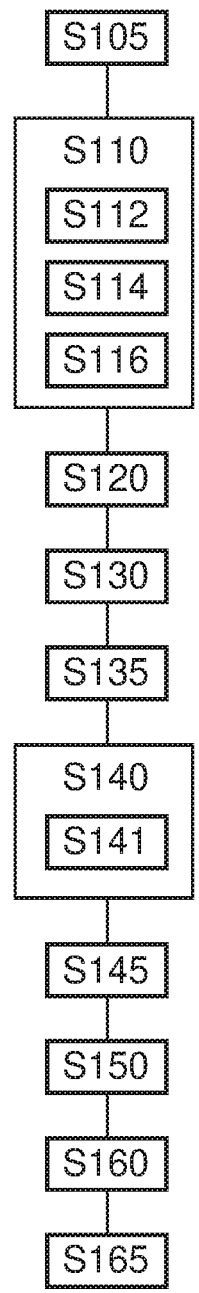
FIG. 15 illustrates a more detailed sequence of steps of a method for operating a computer-assisted surgery device according to an exemplary embodiment of the invention.

FIG. 15 illustrates the method for operating a computer-assisted surgery device in more detail. With this respect, some of the steps illustrated in FIG. 14 may include further sub-steps. With this respect, for example the step of acquiring a three-dimensional image S110 may further include acquiring a first and a second bi-planar image S112. Further, step 110 may include a correlation of the first and second bi-planar image S114 and the step of generating a three-dimensional image S116. These sub-steps are required, if, for example, an imaging unit only provides bi-planar images. However, if an image acquiring unit or an imaging device is capable of directly providing a three-dimensional image, the step S110 does not mandatorily require the sub-steps S112, S114 and S116. The entire method as described along the flow-chart of FIG. 15 starts with bringing the joints of the segmented arms into a fixed state S105 and then acquiring a three-dimensional image S110 as illustrated above. Afterwards, based on the generated three-dimensional image, the method proceeds with acquiring a deviation of the implanting trajectory S120 and with determining a measure of a required motion S130. Then, the joints are brought into a released state S135. It should be noted, that bringing the joint into a released state S135 may also be conducted before step S130 and also before step S120, as the acquisition of the deviation and the determination of the required motion does not depend on the state of the joints. The method then proceeds with controlling a motion of the implant targeting device S140 which may include controlling of the motion of the single segments S141. Afterwards, the joints are brought into a fixed state again in S145. In S150 and S160, a verification can be carried out based on the determined implanting area and the predetermined implanting axis and by again acquiring an image, e.g. a first and second bi-planar image for verification. It should be noted, that S160 may include the same sub-steps as S110 when acquiring a three-dimensional image. Afterwards, the deviation of the predetermined implanting trajectory is determined in S165. It should be noted, that the method further proceeds with determination of the required motion and the controlling of the motion of the robot arms as described above, although it is not illustrated in FIG. 15.

REFERENCE LIST 1 patient
10 bony structure
20 main-implant targeting device
21 reference geometry of main-implant targeting device
22 reference body of main-implant targeting device
23 fiducial markers of main-implant targeting device
24 reference geometry as integral portion of main-implant targeting device
25 implanting trajectory of main-implant targeting device
28 main-implant
29 joining portion of main-implant
30 sub-implant targeting device
31 reference geometry of sub-implant targeting device
32 reference body of sub-implant targeting device
33 fiducial markers of sub-implant targeting device
35 implanting trajectory of sub-implant targeting device
38 sub-implant
40 tool receptacle/tooling device
41 reference geometry of tool receptacle/tooling device
42 reference body of tool receptacle/tooling device
43 fiducial markers of tool receptacle/tooling device
45 tooling trajectory of tool
48 tool
50 sleeve receptacle
51 reference geometry of sleeve receptacle
52 reference body of sleeve receptacle
53 fiducial markers of sleeve receptacle
55 tooling/targeting/guiding trajectory of sleeve
58 sleeve
60 sleeve
61 reference geometry of sleeve
62 reference body of sleeve
63 fiducial markers of sleeve
65 tooling/targeting/guiding trajectory of sleeve
70 K-wire
71 reference geometry of K-wire
72 reference body of K-wire
73 fiducial markers of K-wire
74 reference geometry as integral portion of K-wire
75 tooling trajectory of K-wire
80 drill
81 reference geometry of drill
83 fiducial markers of drill
84 reference geometry as integral portion of drill
85 tooling trajectory of drill
88 (manual) drill tool
100 device for computer-assisted surgery
101 processing unit 110 image acquiring unit
111 correlation unit
112 imaging device
120 deviation acquiring unit
130 motion determining unit
140 motion controlling unit
150 implanting area determining unit
160 position determining unit
170 identification unit for identifying a type of an implant, sub-implant or tool
180 first arm
181 first end of first segmented arm
182 second end of first segmented arm
183 segments of first segmented arm
184 joints between segments of first segmented arm
185 actuators of first segmented arm
190 second segmented arm
191 first end of second segmented arm
192 second end of second segmented arm
193 segments of second segmented arm
194 joints between segments of second segmented arm
195 actuators of second, segmented arm
200 bone data base
F fixed/reference point, mounting point
S105 bringing joints of segmented arm into fixed/locked state
S110 acquiring a three-dimensional image
S112 acquiring a first/second (bi-)planar image
S114 correlating first and second (bi-)planar image
S116 generating three-dimensional image
S120 acquiring a deviation of implanting trajectory
S130 determining a measure of a required motion
S135 bringing joint into released state
S140 controlling a motion of implant targeting device
S141 controlling a motion of segments
S145 bringing joint of segmented arm into fixed/locked state
S150 determining implanting area and predetermined implanting trajectory
S160 acquiring first and second (bi-)planar image for verification
S165 determining deviation of predetermined implanting trajectory

The invention claimed is:

1. A device for computer-assisted surgery, comprising:
a reference structure, a first arm having a first end and a second end, wherein the first end is connected to the reference structure and the second end is connectable to a first implant, in a defined geometrical orientation;
a second arm having a first end, a second end, and a plurality of segments, wherein at least two adjacent segments are coupled with a joint capable of being transitioned from a fixed state to a released state, wherein the first end of the second arm is connected to the reference structure and the second end of the second arm is connectable to a tool in a defined geometrical orientation with respect to a tooling trajectory of the tool, a position determining unit adapted for determining a required position and orientation of the connected tool having the tooling trajectory for bringing the tooling trajectory of the tool into a direction, so that the tooling trajectory of the tool corresponds to a joining portion of the first implant with the tool, a motion controlling unit adapted to transition the second arm from the fixed state to the released state for controlling a motion of the second arm based on a measure of required motion determined by the position determining unit, wherein the motion controlling unit is adapted to transition the second arm from the released state to the fixed state.

2. A device according to claim 1, wherein the first arm and the second arm have position sensors capable of providing positional information to determine a the relative position of the second end of the first arm and the second end of the second arm, wherein the position sensors are located at the connecting joints between respective segments of the first and second arm, and between the first and second arm and their respective reference structure.

3. A device according to claim 1, wherein the first arm has a at least two segments and a connecting joint between two adjacent segments, wherein the connecting joint is capable of being transitioned from a fixed state to a released state and vice versa.

4. A device according claim 3, wherein at least one of the reference geometries has a unique projection pattern for each projection direction.

5. A device according claim 3, wherein at least one of the reference geometries has a plurality of fiducial markers, wherein each of the plurality of fiducial markers has a spatial arrangement having a unique projection pattern for each projection direction.

6. A device according to claim 1, wherein the second end of the first arm has a reference geometry connected thereto and the second end of the second arm has a reference geometry connected thereto.

7. A device according to claim 1, wherein the tool is a drilling tool or a guiding sleeve for a drill and the tooling trajectory is a drilling direction toward a joint of the first implant.

8. A device for computer-assisted surgery, comprising:
a reference structure, a first arm having a first end and a second end, wherein the first end is connected to the reference structure and with the second end is connectable to a first implant, in a defined geometrical orientation;
a second arm having a first end, a second end, and a plurality of segments, wherein at least two adjacent segments are coupled with a joint capable of being transitioned from a fixed state to a released state, wherein the second arm with the first end of the second arm is connected to the reference structure and with the second end of the second arm is connectable to a second implant in a defined geometrical orientation with respect to an implantation trajectory of the second implant, a position determining unit adapted for determining a required position and orientation of the connected second implant having the implantation trajectory for bringing the implantation trajectory of the second implant (38) into a direction, so that the implantation trajectory of the second implant corresponds to a joining portion of the first implant with the second implant, a motion controlling unit adapted to transition the second arm from the fixed state to the released state for controlling a motion of the second arm based on a measure of required motion determined by the position determining unit (160), and for bringing the second arm (190) from the released state into the fixed state.

9. A device according to claim 8, wherein the device has an identification unit for identifying the connected first implant with respect to its geometry, wherein the position determining unit is adapted to determine a required position and orientation of the connected tool and the second implant, respectively, based on an identified geometry of the first implant.

10. A device for computer-assisted surgery, comprising:
a reference structure, a first arm having a first end and a second end, wherein the first end is connected to the reference structure and the second end is connectable to a main implant, in a defined geometrical orientation; a second arm having a first end and a second end, wherein the first end of the second arm is connected to the reference structure and the second end of the second arm is connectable to a guiding device in a defined geometrical orientation with respect to a guiding trajectory of the guiding device,
an identification unit adapted for identifying a main implant having a joining portion connected to the second end of the first arm, a position determining unit adapted for determining a required position and orientation of a connected guiding device having the guiding trajectory based on a stored geometry of the identified main implant and its joining portion for bringing the guiding trajectory of the guiding device into a direction, so that the guiding trajectory of the guiding device corresponds to a joining portion of the main-implant having a device to be guided, a motion controlling unit adapted for controlling a motion of the second arm based on a stored geometry of the identified main implant, the joining portion, and a measure of required motion determined by the position determining unit for bringing the guiding trajectory of the guiding device into a direction so that the guiding trajectory of the device to be guided corresponds to the joining portion of the main implant.

11. A device for computer-assisted surgery according to claim 10, wherein the identification unit is connected to a human interface for entering a main implant identifier allowing the identification unit to identify the main implant and its corresponding geometry from a database.

12. A device for computer-assisted surgery according to claim 10, wherein the identification unit is connected to an image acquiring unit for receiving imaging data of a connected main implant, wherein the identification unit comprises an image recognition unit being adapted for recognition and identification of the main implant for identifying the main implant and its corresponding geometry from a database.

13. A device for computer-assisted surgery according to claim 10, wherein the second arm has a plurality of segments, wherein at least two adjacent segments are coupled with a joint capable of being transitioned from a fixed state to a released state and vice versa, wherein the motion controlling unit is adapted to transition the second arm from the fixed state to the released state, for controlling a motion of the second arm based on a measure of required motion determined by the position determining unit, and adapted to transition the second arm from the released state to the fixed state.

14. A device according to claim 13, wherein the first arm has at least one actuator, each being adapted to controllably actuate a motion of two adjacent segments with respect to each other along the connecting joint of two adjacent segments.

15. A device according to claim 10, wherein the guiding device comprises a reference geometry connected thereto.

16. A device according to claim 10, wherein the guiding device comprises a sleeve having a longitudinal through hole defining the guiding trajectory of the guiding device.

17. A device according to claim 10, wherein the guiding device is adapted to guide a drill.

18. A device according to claim 10,
further comprising a deviation determining unit capable of determining a spatial deviation of a present relative position of the guiding device and one of a tool, a K-wire and a drill guided by the guiding device and a spatial deviation of an intended position of the guiding device and one of a tool, a K-wire and a drill guided by the guiding device based on reference geometries provided with the guiding device, the tool to be guided, the K-wire to be guided and the drill to be guided.

19. A device for computer-assisted surgery, comprising:
a reference structure,
a first arm having a first end and a second end, wherein the first end is connected to the reference structure and the second end is connectable to a first implant, in a defined geometrical orientation;
a second arm having a first end and a second end, wherein the first end is connected to the reference structure and the second end is connectable to a tool in a defined geometrical orientation with respect to a tooling trajectory of the tool,
an identification unit adapted for identifying the first implant with a joining portion connected to the second end of the first arm,
a position determining unit adapted for determining a required position and orientation of a connected tool having the tooling trajectory based on a stored geometry of the first implant and the joining portion for bringing the tooling trajectory of the tool into a direction, so that the tooling trajectory of the tool corresponds to the joining portion of the first implant,
a motion controlling unit adapted for controlling a motion of the second arm based on the stored geometry of the first implant and the joining portion and a measure of required motion determined by the position determining unit for bringing the tooling trajectory of the tool into the direction, so that the tooling trajectory of the tool corresponds to the joining portion of the first implant.

20. A device for computer-assisted surgery, comprising:
a reference structure,
a first arm having a first end and a second end, wherein the first end is connected to the reference structure and the second end is connectable to a first implant, in a defined geometrical orientation;
a second arm having a first end and a second end, wherein the first end is connected to the reference structure and the second end is connectable to a second implant in a defined geometrical orientation with respect to an implantation trajectory of the second implant,
an identification unit adapted for identifying the first implant with a joining portion connected to the second end of the first arm,
a position determining unit adapted for determining a required position and orientation of a connected second implant having the implantation trajectory based on a stored geometry of the first implant and the joining portion for bringing the implantation trajectory of the second implant into a direction, so that the implantation trajectory of the second implant corresponds to the joining portion of the first implant,
a motion controlling unit adapted for controlling a motion of the second arm based on the stored geometry of the first implant and the joining portion and a measure of required motion determined by the position determining unit for bringing the implanting trajectory of the second implant into the direction, so that the implantation trajectory of the second implant corresponds to the joining portion of the first implant.

\* \* \* \* \*